(12) United States Patent
Keady

(10) Patent No.: US 8,631,801 B2
(45) Date of Patent: Jan. 21, 2014

(54) PRESSURE REGULATING SYSTEMS FOR EXPANDABLE INSERTION DEVICES

(75) Inventor: John Patrick Keady, Boca Raton, FL (US)

(73) Assignee: Personics Holdings, Inc, Boca Raton, FL (US)

( * ) Notice: Subject to any disclaimer, the term of this patent is extended or adjusted under 35 U.S.C. 154(b) by 790 days.

(21) Appl. No.: 12/497,894

(22) Filed: Jul. 6, 2009

(65) Prior Publication Data

US 2010/0002897 A1 Jan. 7, 2010

Related U.S. Application Data

(60) Provisional application No. 61/078,406, filed on Jul. 6, 2008.

(51) Int. Cl.
*A61F 11/00* (2006.01)

(52) U.S. Cl.
USPC ............ 128/865; 381/328; 137/843; 137/512

(58) Field of Classification Search
USPC ......................................................... 128/864
See application file for complete search history.

(56) References Cited

U.S. PATENT DOCUMENTS

| | | | |
|---|---|---|---|
| 2,535,258 A | 12/1950 | Bland | |
| 3,602,654 A * | 8/1971 | Victoreen | 181/135 |
| 4,133,984 A * | 1/1979 | Akiyama | 381/328 |
| 4,741,344 A | 5/1988 | Danby et al. | |
| 4,834,211 A * | 5/1989 | Bibby et al. | 181/135 |
| 4,896,679 A | 1/1990 | St. Pierre | |
| 4,962,537 A | 10/1990 | Basel et al. | |
| 5,333,622 A | 8/1994 | Casali et al. | |
| 5,483,027 A | 1/1996 | Krause | |
| 6,094,494 A * | 7/2000 | Haroldson | 381/328 |
| 6,256,396 B1 | 7/2001 | Cushman | |
| 6,339,648 B1 | 1/2002 | McIntosh et al. | |
| 6,393,130 B1 | 5/2002 | Stonikas et al. | |
| 6,671,381 B1 | 12/2003 | Lux-Wellenhof | |
| 7,130,437 B2 | 10/2006 | Stonikas et al. | |
| 7,164,775 B2 | 1/2007 | Meyer et al. | |
| 7,227,968 B2 | 6/2007 | van Halteren et al. | |
| 7,362,875 B2 | 4/2008 | Saxton et al. | |
| 7,387,187 B2 | 6/2008 | Widmer et al. | |
| 7,861,723 B2 * | 1/2011 | Dedrick et al. | 128/848 |
| 8,047,207 B2 * | 11/2011 | Perez et al. | 128/864 |
| 2002/0055690 A1 | 5/2002 | Want et al. | |
| 2006/0159298 A1 | 7/2006 | von Dombrowski et al. | |
| 2007/0116319 A1 | 5/2007 | Hagberg | |
| 2008/0144871 A1 | 6/2008 | Purcell et al. | |
| 2009/0028356 A1 * | 1/2009 | Ambrose et al. | 381/71.6 |
| 2009/0173353 A1 * | 7/2009 | Purcell et al. | 128/865 |
| 2009/0320858 A1 | 12/2009 | Purcell et al. | |
| 2009/0320859 A1 | 12/2009 | Purcell et al. | |

OTHER PUBLICATIONS

International Search Report for International Application No. PCT/US2009/049696, dated Dec. 10, 2009.

* cited by examiner

*Primary Examiner* — Patricia Bianco
*Assistant Examiner* — Raymond E Harris

(57) ABSTRACT

Earpieces and expandable insertion devices are provided. An earpiece includes an ambient sound microphone (ASM); an ear canal microphone (ECM); an ear canal receiver (ECR); and an inflatable sealing section. The sealing section includes at least one pressure valve. The at least one pressure valve opens when the pressure in the sealing section is greater than an ambient pressure.

16 Claims, 5 Drawing Sheets

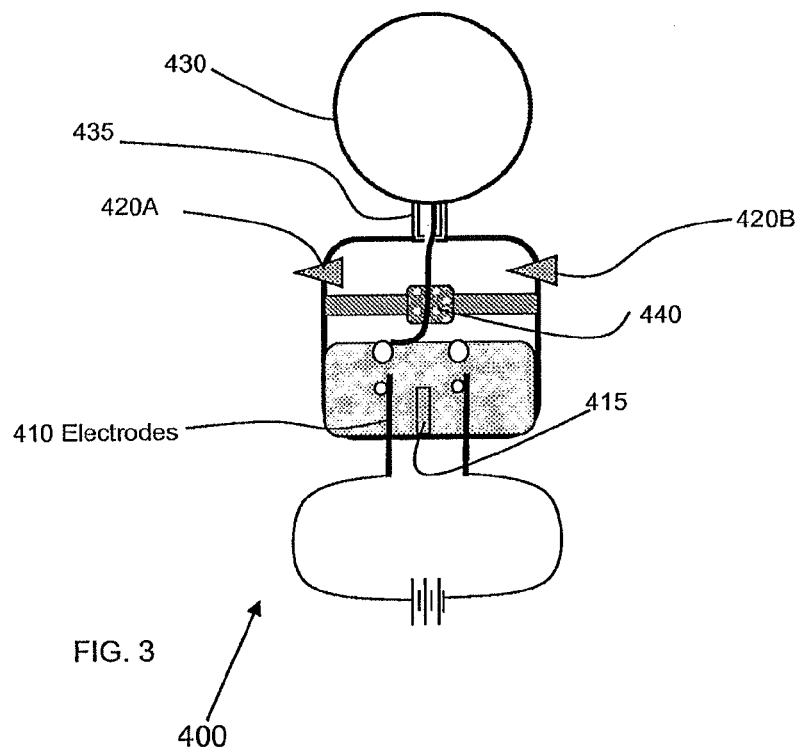
FIG. 3
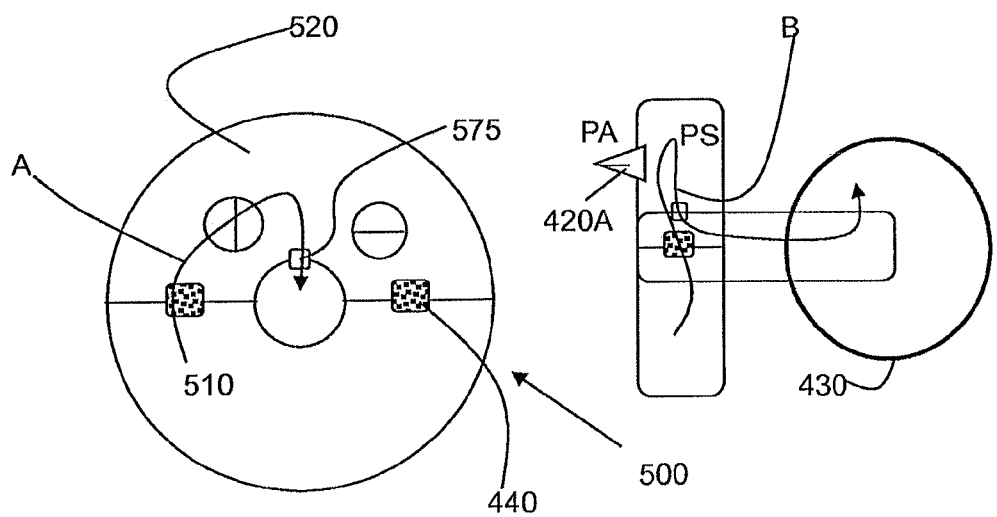
FIG. 4A
FIG. 4B

US 8,631,801 B2

PRESSURE REGULATING SYSTEMS FOR EXPANDABLE INSERTION DEVICES

CROSS-REFERENCE TO RELATED APPLICATIONS

This application claims the benefit of U.S. provisional patent application No. 61/078,406 filed 6 Jul. 2008. The disclosure of which is incorporated herein by reference in its entirety.

FIELD OF THE INVENTION

The present invention relates to devices that can be inserted into orifices where upon insertion a sealing section's pressure can be regulated.

BACKGROUND OF THE INVENTION

Sealing an orifice has taken many forms in the past. Using a pressurized sealing system can result in challenges, which can arise when coupled to a commercial device. One of these challenges is to maintain a level of pressure of sealing so as not to exceed a threshold value. An innovative method is needed to facilitate pumping of the sealing section along with pressure regulation.

SUMMARY OF THE INVENTION

At least one exemplary embodiment is directed to a pressure regulation system, comprising: an inflatable sealing section configured to seal a user's orifice; and a pressure management system operatively connected to the sealing section, where the pressure management system includes at least one pressure valve, where the pressure valve is configured to open when an absolute value of the pressure difference between a sealing section pressure and a reference pressure is greater than a threshold value.

An example embodiment is directed to an orifice insertion device. The orifice insertion device includes an insertion element including a feeding tube; an expandable element configured to seal an orifice; a pressure regulation system coupled to the insertion element; and a pressure release mechanism coupled to the pressure regulation system. The expandable element includes an interior region at a first pressure. The expandable element is circumferentially attached to the insertion element and is coupled to the feeding tube. The pressure regulation system includes at least one pressure valve. The pressure regulation system is configured to provide a medium to the interior region of the expandable element via the feeding tube of the insertion element responsive to the at least one pressure valve. The pressure regulation system has a second pressure proximate the at least one pressure valve. The pressure release mechanism is configured to manually adjust a current pressure in the expandable element responsive to a user. The pressure release mechanism includes a release pin coupled to the at least one pressure valve and a resilient restoring member coupled to the release pin. The resilient restoring member includes an elastic membrane. Activation of the resilient restoring member decreases the current pressure in the expandable element. The at least one pressure valve is configured to open to at least a design flow rate when a difference between the first pressure and the second pressure is greater than a threshold level.

At least one exemplary embodiment is directed to an earpiece comprising: an ambient sound microphone (ASM); an ear canal microphone (ECM); an ear canal receiver (ECR); and an inflatable sealing section, where the sealing section includes at least one pressure valve, where the at least one pressure valve opens when the pressure in the sealing section is greater than an ambient pressure.

BRIEF DESCRIPTION OF THE DRAWINGS

Exemplary embodiments of the present invention will become more fully understood from the detailed description and the accompanying drawings, wherein:

FIG. 3 illustrates at least one method of inflating an inflatable device and a pressure management system in accordance with at least one exemplary embodiment;

FIGS. 4A and 4B are front view and side view diagrams, respectively, illustrating a non-limiting example of a pressure management system;

DETAILED DESCRIPTION OF EXEMPLARY EMBODIMENTS OF THE PRESENT INVENTION

Figure 1:
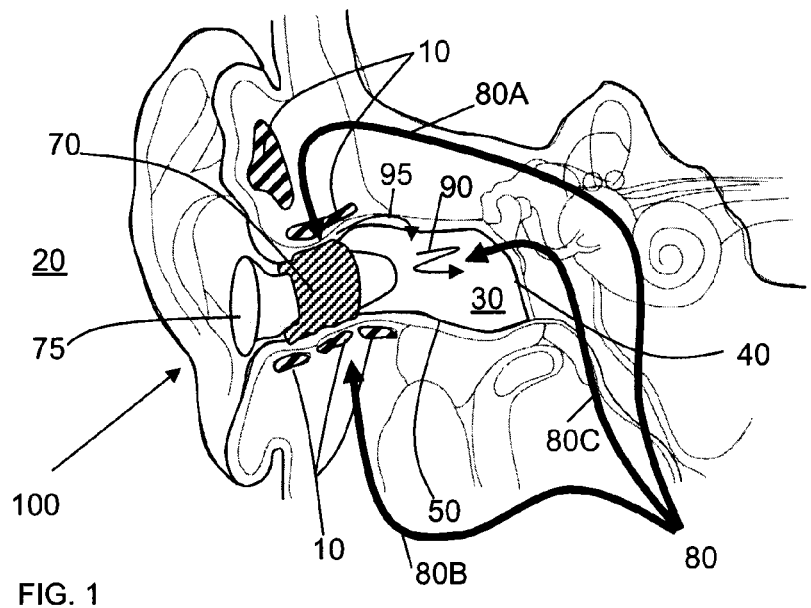
FIG. 1 illustrates an ear canal as a non-limiting example of an orifice that can be sealed forming a resonance chamber.

The following description of exemplary embodiment(s) is merely illustrative in nature and is in no way intended to limit the invention, its application, or uses.

Exemplary embodiments are directed to or can be operatively used on various wired or wireless earpiece devices (e.g., earbuds, headphones, ear terminal, hearing aids, behind the ear devices, or other acoustic devices as known by one of ordinary skill in the art, and equivalents) or other devices that can be inserted into other orifices, e.g., pipes, veins.

Processes, techniques, apparatus, and materials as known by one of ordinary skill in the art may not be discussed in detail but are intended to be part of the enabling description where appropriate. For example material fabrication may not be disclosed, nor attachment procedures (e.g., adhesive attaching of separate ridge structures), but such, as known by one of ordinary skill in such arts is intended to be included in the discussion herein when necessary. For example if an orifice insertion device includes a valve or an expandable element uses a particular fluid (e.g., liquid or gas) and the design criteria is for the device to maintain a level of pressure for a period of time, then the material (composition and/or thickness) used for the valves, expandable element (e.g., balloon) and other pneumatic support systems (e.g., feed tubes, release systems, device cavities at pressure) will have to have the permeability properties to maintain the pressure levels designed for.

Notice that similar reference numerals and letters refer to similar items in the following figures, and thus once an item is defined in one figure, it may not be discussed or further defined in the following figures.

FIG. 1 illustrates a sealed (occluded) ear canal 50, with a sealed volume 30 (sealed from receiving sound from ambient environment 20). Voice can leak 80 into the sealed volume 30 between insertion element 75 and eardrum 40 from various source paths 80A, 80B, and 80C. Source paths 80A and 80B represent sound conducted from bones 10 adjacent to ear canal 50. Source path 80C represents sounds 90, 95 to ear canal 50 from other areas of the ear. In one explanation, the leaked acoustic energy results in an amplification (e.g., by resonance) at certain frequencies within the sealed volume 30, resulting in the Occlusion Effect. If the ear canal 50 (a non-limiting example of an orifice) was unsealed then no resonance could build and hence there would be no Occlusion Effect. While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments.

FIG. 1 illustrates at least one exemplary embodiment. An earpiece 100 can include an insertion element 75 operatively connected to a sealing section. The sealing section can include an expandable element 70 (e.g., expanding polymers, inflatable systems, mechanically expanded systems). Although an earpiece 100 is illustrated any orifice inserted device can be included in exemplary embodiments. By orifice what is meant is any organic and non-organic opening that can be filled such as veins, arteries, ear canals, chest cavities, noses, pipes, and other similar orifices.

Figure 2:
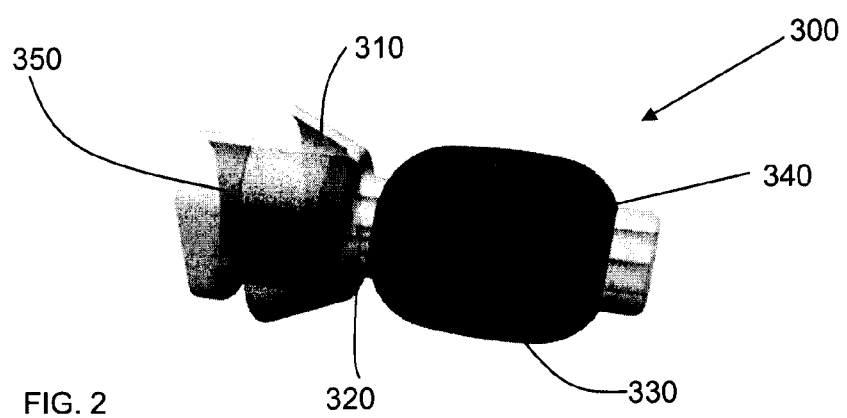
FIG. 2 illustrates an inflatable device in accordance with at least one exemplary embodiment.

FIG. 2 illustrates an inflatable system 300 comprising an insertion element 320 (e.g., a multi-lumen tube) and an expandable element 330 (e.g., a urethane balloon, a nylon balloon). The expandable element 330 can be filled with an expanding medium (e.g., a gas, a liquid, an electroactive polymer and/or a gel) fed via a supply tube 340. The device illustrated in FIG. 2 illustrates a flange 310 designed to stop at a designated position in the orifice (e.g., at the opening of the orifice), and an instrument package 350 can include additional devices and equipment to support expansion control (e.g., a power supply and leads, gas and/or fluid generation systems).

FIG. 3 illustrates at least one exemplary system 400 for pressure generation and control. The non-limiting example illustrated includes a balloon 430 operatively attached to a catheter 435 at least one pressure control valve (e.g., valve 420A, valve 420B); electrodes 410, a porous plug 440 (e.g. micro pore plastics that allow gas to pass but block fluid motion), and optionally a membrane 415 (e.g., Nafion™) that absorbs the electrolysis medium (e.g., $H_2O$ with NaCl dissolved at 0.001 mole/liter) allowing a current to pass between the electrodes 410 as if the electrodes 410 were essentially in free electrolysis material, and at the same time preventing the electrodes 410 from touching. The membrane 415 facilitates close placement of the electrodes 410 increasing the electric field and hence the current. As illustrated the seal pressure value is as discussed above, the operating pressure is some value greater than the seal pressure value (e.g., 20% greater) at which an expandable element operates for a given condition. FIG. 3 illustrates an electrolysis system where the gas generated passes through a porous plug 440 into a chamber that has control valves 420A, 420B. The control valves 420A, 420B are designed to allow a certain gauge pressure value to be reached inside the chamber (e.g., 50% gauge) while allowing gas from the outside of the chamber to enter if the gauge pressure value drops below a value (e.g., −50% gauge), where the gauge pressure in this instance is calculated as the pressure inside the chamber minus the pressure outside the chamber.

FIGS. 4A and 4B are front view and side view diagrams, respectively, illustrating a non-limiting example of a pressure management system 500 for an earpiece. A pressure generator 510 (e.g., a system as illustrated in FIG. 3) can be configured to generate gas (e.g., $H_2$ and $O_2$ from electrolysis). The gas can travel (e.g., front view A, side view B) through a porous plug 440 that allows gas to penetrate but discourages liquids. This gas accumulates in the pressure manifold 520, and passes through a feed tube 575 through a stent into the inflatable sealing section (e.g., balloon 430). The pressure manifold 520 can include several valves (e.g., valve 420A) that can be used to regulate the pressure in the pressure manifold 520. Thus when the pressure PS inside the pressure manifold 520 is greater than an ambient value PA the valve(s) (e.g., valve 420A) can be designed to open equalizing the pressures to a preset difference value, for example |PS-PA|<0.1 atm. Note that the size of the pressure management system 500 can be the size of a flange (e.g., outer diameter of about 10 mm). The pressure management system 500 can be constructed of various materials and can additionally include a sealing coating or bladder to help maintain pressure within the various sections (e.g., pressure generator 510, pressure manifold 520).

Although not mentioned to this point, the electrodes 410 (FIG. 3) can vary in shape and relative size. For example the electrode producing more gas (e.g., the electrode associated with H formation in water) can be made large in surface area facilitating more formation area. Additionally the electrodes 410 (FIG. 3) can be separated by an electrolysis medium absorber (e.g., Nafion, membrane 415). Note that the electrode material can vary, for example conductive material that will not oxidize in the electrolysis medium (e.g., stainless steel, platinum, gold).

At least one exemplary embodiment is directed to a pressure regulation system, comprising: an inflatable sealing section (e.g., balloon with fluid and/or gas, electroactive polymers including gels, chemical gas reactions) configured to seal a user's orifice (e.g., ear canal, nose, anus, vein, artery, chest cavity, heart valve region); and a pressure management system (e.g., a system with passive or active valves) operatively connected to the sealing section, where the pressure management system includes at least one pressure valve, where the pressure valve is configured to open when an absolute value of the pressure difference between a sealing section pressure and a reference pressure is greater than a threshold value.

At least one exemplary embodiment is directed to an earpiece (such as earpiece 623 shown in FIG. 6) comprising: an ambient sound microphone (ASM) (e.g., ASM 625 in FIG. 6); an ear canal microphone (ECM) (e.g., ECM 626 in FIG. 6); an ear canal receiver (ECR) (e.g., ECR 624 in FIG. 6); and an inflatable sealing section, where the sealing section includes at least one pressure valve, where the at least one pressure valve opens when the pressure in the sealing section is greater than an ambient pressure. The system can be used as a reference pressure for an ambient pressure. The system can use various threshold values, for example a threshold value of about 10% of the reference pressure. Additionally the system can use the sealing section pressure for determining the threshold value, for example the threshold value can be about 10% of the sealing section pressure.

Figure 5:
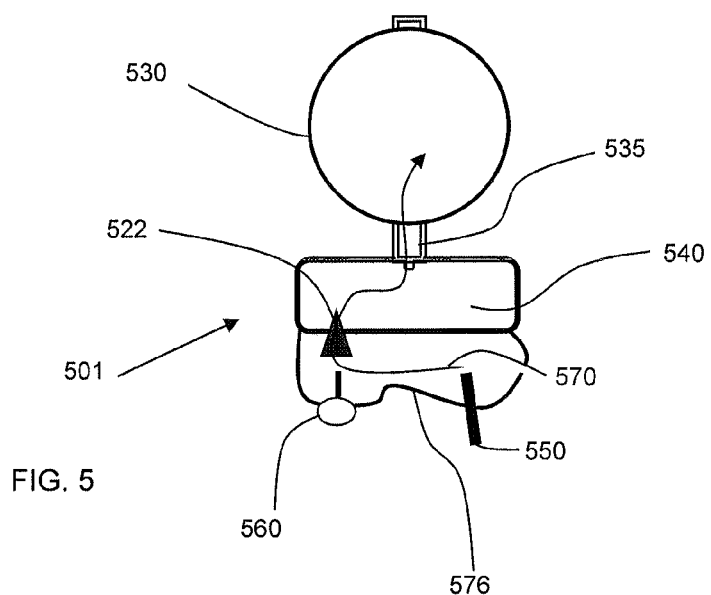
FIG. 5 illustrates a non-limiting example of a manual pump system attached to an earpiece in accordance with at least one exemplary embodiment.

FIG. 5 illustrates a non-limiting example of a manual pump system attached to an orifice insertion device in accordance with at least one exemplary embodiment. For example the orifice insertion device can be an earpiece 501. The earpiece 501 can include an expandable element 530 (e.g., balloon) operatively attached to a catheter 535. The catheter 535 can have a pneumatic tube to carry internal medium (e.g., air) from a pump 576 to the expandable element 530. The pump 576 can have various designs (e.g., automatic (e.g., electrolysis), or manual). Illustrated in FIG. 5 is a non-limiting example of a manual pump 576, including a body, a hole 550 that is covered during pressing, and a release pin 560. The pumped fluid 570 then can travel directly into the pneumatic tube or through a pressure manifold 540, to which other release valves 522 can be attached. Note that the catheter 535 can be a multi-lumen tube where one of the lumen is the pneumatic tube, and other lumen(s) serve other purposes, for example one may be attached to a microphone to sample the acoustic environment near the tip of the catheter 535.

Figure 6:
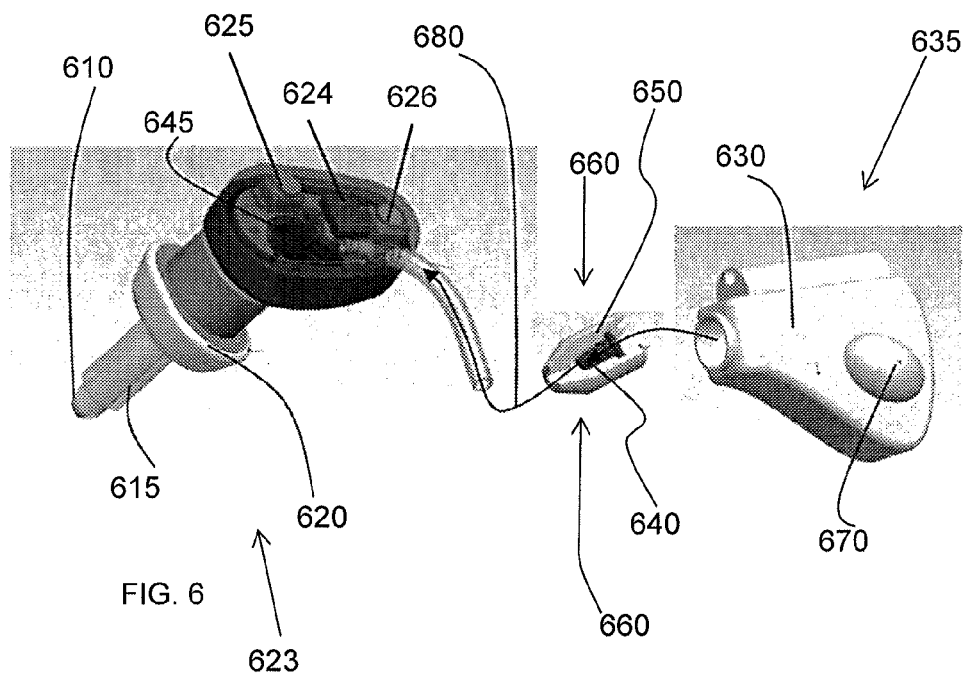
FIG. 6 illustrates at least one exemplary embodiment where a manual pump, attachable to a headphone cable, is operatively connected to an inflatable earpiece.

FIG. 6 illustrates at least one exemplary embodiment where a manual pump 635, attachable to a headphone cable is operatively connected to an inflatable earpiece 623. In this non-limiting example a pump 635 (e.g., manual or automatic) can be separate from the earpiece 623. The earpiece 623 and the pump 635 can be pneumatically coupled so that the fluid 680 flows from the pump 635 to the earpiece 623. The manual pump 635 illustrated can include a hole intake 670, which is pressed and covered during pumping, a body 630 that can include a cable clip, and a valve 640 surrounded by a valve housing 650. The valve 640 can be a flexible valve (e.g., flexible material duck valve) and the valve housing 650 flexible so that both can be squeezed 660 to release the pressure. The earpiece can include a catheter 610, a balloon 615 attached to the catheter 610, a stop flange 620 (e.g., to control insertion depth), and an optional release valve 645, to release pressure when the internal pressure of the expandable element (e.g., balloon) exceeds a certain level (e.g., 1.4 atm absolute pressure).

Figure 7:
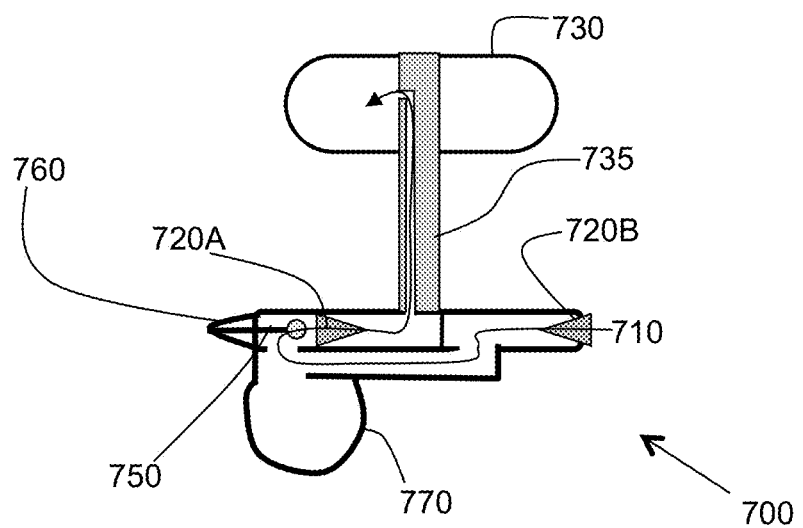
FIG. 7 illustrates at least one exemplary embodiment of a manual pump system attached to an earpiece with another valve arrangement according to at least one exemplary embodiment.

FIG. 7 illustrates at least one exemplary embodiment of a manual pump system attached to an earpiece 700 with another valve arrangement according to at least one exemplary embodiment. The inflation management system (IMS) (e.g., pumps, pneumatic tubes, expandable elements, and valves) can include various valve configurations and designs. The IMS illustrated in FIG. 7 includes a refill valve 720B, and a valve 720A with optional release mechanism. The optional release mechanism can include a resilient (e.g., elastic membrane, molded rubber shape with a restoring force) restoring member 760 operatively attached to a release pin 750. The restoring member 760 can be pressed to actuate the release pin 750 (e.g., movement in millimeters) to effectuate (e.g., facilitate) the opening of valve 720A to decrease the pressure in the expandable element 730 (e.g., balloon). The expandable element 730 can be fed via a pneumatic tube coupled to a pump system (e.g., which can include a pump bladder 770). The pneumatic tube can travel through a catheter 735. Note the restriction on materials for the pneumatic systems (pneumatic tube, expandable element, valves) that keep the expandable element 730 pressurized depend upon design criteria. For example if a design criteria is to use ambient air and maintain a gauge pressure greater than 0.4 atm over a period of 16 hours, then the permeability of the materials used need to be taken into consideration. In addition the orifice that the device is to be inserted must also be taken into account. For example if the orifice is an ear canal then the material which satisfies the permeability must also satisfy the flexibility to avoid irritation and achieve bending through the ear canal. Note silicon, while having desirable characteristics in flexibility presents challenges in permeability. One of ordinary skill in the arts will be able to determine without undue experimentation which extrudable or moldable flexible material can be used to satisfy the permeability and flexibility criteria. For example Teflon has a favorable permeability, and can be used as a balloon as well, although not flexible it can be designed for a certain size.

Figure 8:
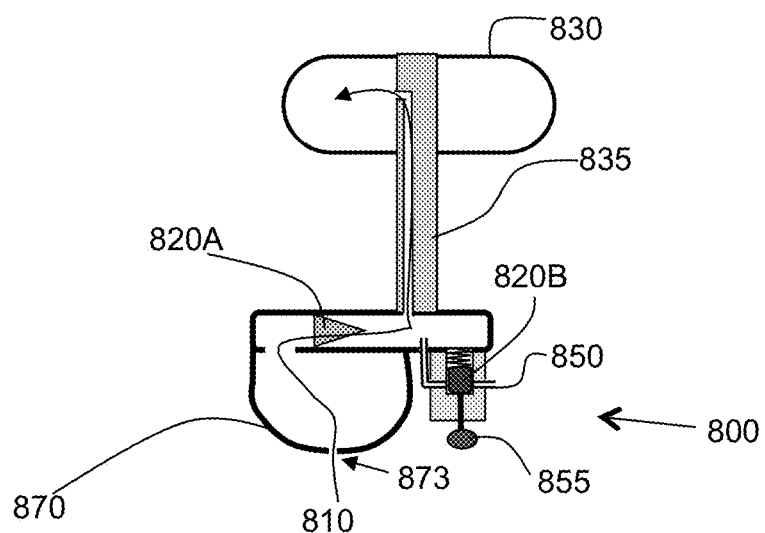
FIG. 8 illustrates at least one exemplary embodiment of a manual pump system attached to an earpiece with another valve arrangement according to at least one exemplary embodiment.

The operation of the earpiece illustrated in FIG. 7 is straightforward. The pump bladder 770 is pressed, by which pumped air 710 is passed through valve 720A. Note that valve 720B prevents the pumped air 710 from passing out. After the pumped air 710 passes through valve 720A, the pump bladder 770 can be designed to re-expand, thus pulling new air through valve 720B into the pump bladder 770 for subsequent pumps. To facilitate re-expanding of the pump bladder 770, the pump bladder 770 can be made of a flexible material that can be depressed but has a resilience to move back to its original shape (e.g., a dimple of rubber). This particular design facilitates rapid pumping since air will flow back into the pump bladder 770 upon lifting of the finger. FIG. 8 illustrates another design having a hole 873 that can be covered by a finger. This design requires the filling of the pump bladder 870 to occur through a hole 873. Thus the pumping action is dependent upon the refill time through the hole 873.

FIG. 8 illustrates at least one exemplary embodiment of a manual pump system attached to an earpiece 800 with another valve arrangement according to at least one exemplary embodiment. In the non-limiting example illustrated air 810 flows through a hole 873 in the pump bladder 870. When the pump bladder is depressed (e.g., via finger, actuator) the depressor (e.g., finger, actuator) covers at least a large portion of the hole 873 so that upon depression the air in the bladder 870 is forced through the valve 820A, through a pneumatic tube in a catheter 835, and into an expandable member 830 (e.g., balloon). A release valve can take many forms as discussed herein, and an example is illustrated in FIG. 8. A flexible tube 850 is operatively attached to an interior of expandable element 830, the flexible tube 850 then runs through a depression channel that can be closed by pressure from a spring actuated release valve 820B. For example when pressure (e.g., compression of the tubing via a spring loaded piston) is applied to the flexible tube 850, the tube 850 can seal prohibiting release of pressure in the interior of the expandable element 830 (e.g., sealing section pressure). When release is desired the release button 855 can be pulled (spring loaded piston pressing against the tube 850 toward the catheter 835 to close thus pulling to open) or pushed (spring loaded piston pressing against the tube 850 toward the hole 873 to close thus pushing to open).

Figure 9A:
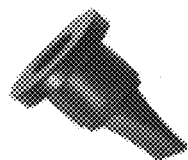
FIGS. 9A-9D illustrate various non-limiting examples of valves that can be used in various configurations in accordance with at least one exemplary embodiment.
Figure 9B:
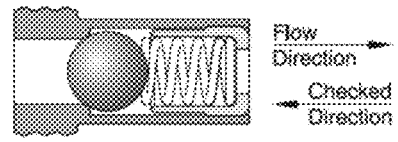
Figure 9C:
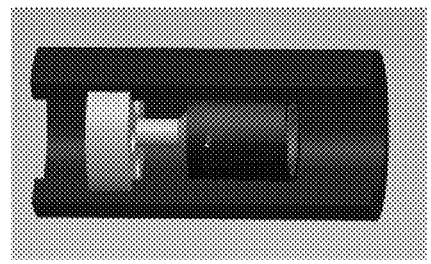
Figure 9D:
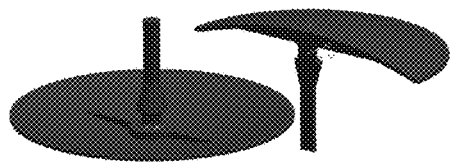

FIGS. 9A-9D illustrate various non-limiting examples of valves that can be used in various configurations in accordance with at least one exemplary embodiment. The valves illustrated are non-limiting and for illustrative purposes only. The first valve is a loaded duckbill valve (can also be non-leaded) (FIG. 9A), the second valve is a ball and spring valve (FIG. 9B), the fourth valve is a umbrella valve (FIG. 9D), and FIG. 9C is a one way valve using two concentric tubes (referred to as a sheath valve), where the pressure on the right compresses the tubes into each other prohibiting backflow (to the left of the figure) through the valve. Flow from the left to right travels between the two concentric tubes when the design pressure on the left is greater than the pressure on the right by a chosen amount (e.g., left pressure 1.5 atm, pressure on left 1.4 atm). Note other valves can be used, for example flapper valves.

Note that several configurations illustrate gas as the expanding and/or displaced medium. Note that other exemplary embodiments can use the same configuration for liquids.

At least one exemplary embodiment is directed to an orifice insertion device (e.g., an earpiece, a device for insertion into a pipe, a device for insertion into any channel for example a vein, a device for insertion into other body orifices, a device for insertion into a hole, for example a hole in a wall or plate, or a hole in a floor, and other systems or cavities where a device can be inserted into a recess) including a pressure regulation system (e.g. a system that can actively or passively control a pressure range in an interior pressure environment).

The orifice insertion device can include an expandable element configured to seal an orifice. For example the expandable element can be an expanding gel, an electroactive polymer (e.g., IPMC), a stressed membrane (e.g., a stretched membrane), a balloon, an expanding flange with an interior pressureable system, and expanding foam with an interior pressureable system. The orifice insertion device can include at least one pressure valve, where the expandable element includes an interior region (e.g., inside a balloon) including an interior medium (e.g., air or liquid), where the interior medium has a first pressure (e.g., 1.2 to 2 bar absolute), where the orifice insertion device is in at least a first medium (e.g., ambient air) and where at least a first portion (e.g., if inserted into an ear then the first portion can be the side closest to the ear drum or the side farthest from the ear drum) of the first medium has a second pressure (e.g., 1 atm, ambient pressure), and where the at least one pressure valve is configured to open to at least a design flow rate (e.g., 0.1 cc/min) when the difference between the first and second pressure is greater than a threshold level (e.g., between 0.1 and 1.0 bar).

Note that the interior medium can includes at least one of air, electrolysis gas, water, oil and glycerin.

Note that in at least one exemplary embodiment the one pressure valve can be configured so that flow into the interior region is larger than out of the interior region when the difference is greater than the threshold value. For example when the pumped air is at 1.5 atm and the interior air is at 1.0 atm, then the valve can be chosen so that the air flow into the interior region is larger than the flow out so that the net effect is that the interior region pressure increases, or is larger in volume or both. Additional embodiments can include a release valve as discussed previously where the release valve is configured so that flow out of the interior region is larger than that into the interior region when the difference is greater than a second threshold value (e.g., when the pressure in the interior region exceeds a gauge pressure of 0.2 bar to 1.0 bar).

In at least one exemplary embodiment the first medium can be from a pump where the fluid flows from the pump to the interior region when the difference in pressure between the first medium (e.g., air in a pump bladder) and the interior medium is greater than the threshold value (e.g. 0.1 bar to 1.0 bar).

In at least one further exemplary embodiment a release valve can be included where the release valve is configured so that flow out of the interior region is larger than that into the interior region when the difference in pressure between the interior medium and an ambient medium is greater than a second threshold value (e.g., gauge pressure between 0.1 and 1 bar). For example the threshold value can be 10 to 50% of the interior medium pressure and/or the ambient pressure.

At least one further exemplary embodiment is where the orifice insertion device is an earpiece. For example at least one exemplary embodiment is an earpiece comprising: an ear canal receiver (ECR); and an inflatable sealing section (e.g., a section including an expandable element or balloon), where the sealing section includes at least one pressure valve, where the at least one pressure valve opens with a designed flow rate when the pressure in the sealing section is greater than a reference pressure by a threshold amount. The earpiece can further include an ambient sound microphone (ASM). Note that non-limiting examples of useable ECRB are the TWFK Knowles receivers, and useable ASMs are mems microphones and FG, TO Knowles microphones. Note many other types, models, manufacturers, and configurations (e.g., armature, diaphragm, mems) can be used and a specific choice will depend on the sampling environment anticipated.

In at least one exemplary embodiment, for example a hearing aid, the acoustic feedback between an ECR and an ASM can be reduced by sealing the region between the two, for example using the inflatable sealing section.

Note also that an ear canal microphone (ECM) can be coupled to the interior region to acoustically sample an in-channel region (e.g., the region near the ear drum), and where the ECM is coupled to an in-channel environment via an acoustic channel.

The description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. An orifice insertion device, comprising:
an insertion element including a feeding tube;
an expandable element configured to seal an orifice, the expandable element including an interior region at a first pressure, the expandable element circumferentially attached to the insertion element and coupled to the feeding tube;
a pressure regulation system coupled to the insertion element, the pressure regulation system including at least one pressure valve, the pressure regulation system configured to provide a medium to the interior region of the expandable element via the feeding tube of the insertion element responsive to the at least one pressure valve, the pressure regulation system having a second pressure proximate the at least one pressure valve; and
a pressure release mechanism coupled to the pressure regulation system, the pressure release mechanism configured to manually adjust a current pressure in the expandable element responsive to a user,
where the pressure release mechanism includes a release pin coupled to the at least one pressure valve and a resilient restoring member coupled to the release pin, the resilient restoring member including an elastic membrane, activation of the resilient restoring member decreasing the current pressure in the expandable element, and
where the at least one pressure valve is configured to open to at least a design flow rate when a difference between the first pressure and the second pressure is greater than a threshold level.

2. The device according to claim 1, where the at least one pressure valve is at least one of a duckbill valve, an umbrella valve, a ball and spring valve, a flapper valve, and a sheath valve.

3. The device according to claim 1, where the medium includes at least one of air, electrolysis gas, water, oil and glycerin.

4. The device according to claim 1, where the at least one pressure valve is configured so that flow into the interior region is larger than out of the interior region when the difference is greater than the threshold level.

5. The device according to claim 1, further comprising a pump coupled to the pressure regulation system, the pump configured to provide the medium to the expandable element via pressure regulation system.

6. The device according to claim 1, where the threshold level is between about 10% and about 40% of the second pressure.

7. The device according to claim 1, where the threshold level is between about 10% and about 40% of the first pressure.

8. An earpiece comprising:
an ear canal receiver (ECR); and
an inflatable sealing section,
where the sealing section includes:
an insertion element including a feeding tube;
an expandable element configured to seal an orifice, the expandable element including an interior region at a first pressure, the expandable element circumferentially attached to the insertion element and coupled to the feeding tube;
a pressure regulation system coupled to the insertion element, the pressure regulation system including at least one pressure valve, the pressure regulation system configured to provide a medium to the interior region of the expandable element via the feeding tube of the insertion element responsive to the at least one pressure valve, the pressure regulation system having a second pressure proximate the at least one pressure valve; and
a pressure release mechanism coupled to the pressure regulation system, the pressure release mechanism configured to manually adjust a current pressure in the expandable element responsive to a user,
where the pressure release mechanism includes a release pin coupled to the at least one pressure valve and a resilient restoring member coupled to the release pin, the resilient restoring member including an elastic membrane, activation of the resilient restoring member decreasing the current pressure in the expandable element, and
where the at least one pressure valve is configured to open to a design flow rate when a difference between the first pressure and the second ressure is greater than a reference pressure by a threshold amount.

9. The earpiece according to claim 8, further comprising:
an ambient sound microphone (ASM).

10. The earpiece according to claim 9, where the inflatable sealing section reduces an occurrence of acoustic feedback between the ASM and the ECR.

11. The earpiece according to claim 8 further comprising:
an ear canal microphone (ECM), where the ECM is coupled to an in-channel environment via an acoustic channel.

12. The earpiece according to claim 11, where the in-channel environment is an inside of an ear canal.

13. The earpiece according to claim 8, where the reference pressure is an ambient pressure.

14. The earpiece according to claim 8, where the reference pressure is a pumping pressure.

15. The earpiece according to claim 8, where the threshold amount is between about 10% and about 40% of the reference pressure.

16. The earpiece according to claim 8, where when the pressure release mechanism is pushed the pressure in the sealing section decreases.

* * * * *